US006660508B1

(12) United States Patent
Cheung

(10) Patent No.: US 6,660,508 B1
(45) Date of Patent: Dec. 9, 2003

(54) DIETARY SUPPLEMENTS FOR TREATING HYPERLIPEMIA

(75) Inventor: Ling Yuk Cheung, Hong Kong (HK)

(73) Assignee: Ultra Biotech Limited, Douglas (GB)

( * ) Notice: Subject to any disclaimer, the term of this patent is extended or adjusted under 35 U.S.C. 154(b) by 0 days.

(21) Appl. No.: 10/187,108

(22) Filed: Jun. 28, 2002

(51) Int. Cl.$^7$ .......................... C12N 13/00; C12N 1/00; C12N 1/14

(52) U.S. Cl. ................. 435/173.1; 435/243; 435/254.1; 435/255.2; 435/255.21; 435/940

(58) Field of Search ............................. 435/173.1, 243, 435/254.1, 255.2, 255.21, 940

(56) References Cited

U.S. PATENT DOCUMENTS

| | | | |
|---|---|---|---|
| 4,081,367 A | 3/1978 | Hulls et al. | 210/610 |
| 4,183,807 A | 1/1980 | Yoshizawa et al. | 210/611 |
| 4,211,645 A | 7/1980 | Zajic et al. | 210/611 |
| 4,559,305 A | 12/1985 | Zajic et al. | 435/243 |
| 4,816,158 A | 3/1989 | Shimura et al. | 210/610 |
| 5,075,008 A | 12/1991 | Chigusa et al. | 210/610 |
| 5,106,594 A | 4/1992 | Held et al. | 422/292 |
| 5,416,010 A | 5/1995 | Langenberg et al. | 435/468 |
| 5,476,787 A | 12/1995 | Yokoyama et al. | 435/262.5 |
| 5,567,314 A | 10/1996 | Chigusa et al. | 210/150 |
| 5,578,486 A | 11/1996 | Zhang | 435/243 |
| 5,707,524 A | 1/1998 | Potter | 210/606 |
| 5,879,928 A | 3/1999 | Dale et al. | 435/264 |
| 6,036,854 A | 3/2000 | Potter | 210/177 |
| 6,391,617 B1 | 5/2002 | Cheung | 435/254 |
| 6,391,618 B1 | 5/2002 | Cheung | 435/255 |
| 6,391,619 B1 | 5/2002 | Cheung | 435/255 |
| 6,436,695 B1 | 8/2002 | Cheung | 435/254 |
| 6,440,713 B1 | 8/2002 | Cheung | 435/173 |
| 2002/0123127 A1 | 9/2002 | Cheung | 435/254.21 |
| 2002/0123129 A1 | 9/2002 | Cheung | 435/254.21 |
| 2002/0123130 A1 | 9/2002 | Cheung | 435/262.5 |

FOREIGN PATENT DOCUMENTS

| | | |
|---|---|---|
| CN | 1110317 A | 10/1995 |
| EP | 0041373 | 12/1981 |
| FR | 2222433 | 10/1974 |
| JP | 60028893 | 2/1985 |
| SU | 415983 A | 11/1974 |
| SU | 1071637 | 2/1984 |
| WO | WO 95/04814 | 2/1987 |
| WO | WO 87/02705 | 5/1987 |
| WO | WO 99/60142 | 11/1999 |
| WO | WO 02/20431 | 3/2002 |
| WO | WO 02/070682 | 9/2002 |

OTHER PUBLICATIONS

Binninger, D. M. et al., "Effects of 60Hz AC magnetic fields on gene expression following exposure over multiple cell generations using Saccharomyces cerevisiae", Bioelectrochemistry and Bioenergetics, 43(1):83–89 (1997).

Deguchi, T. et al., "Nylon biodegradation by lignin–degrading fungi", Applied and Environmental Microbiology, 63(1): 329–331 (1997).

Pichko, V. B. et al., "Electromagnetic stimulation of productivity of microorganisms and its mechanisms", Prikladnaya Biokhimiya I Mikrobiologiya, 32(4): 468–472 (1996).

Ponne, C. T. et al., "Interaction of electromagnetic energy with biological material–relation to food processing", Radiation Physics and Chemistry, 45(4):591–607 (1995).

Van Rensburg, P. et al., "Engineering yeast for efficient cellulose degradation", Yeast, 14(1):67–76 (1998).

"Saccharomyces cerevisiae Meyen ex Hansen", China Catalogue of Cultures/China Committee of Culture Collection for Microorganisms (CCCCM), "www.im.ac.cn/database/YEAST/y122.htm", Apr. 24, 1996, retrieved on Nov. 7, 2002.

K. Asami et al., "Real–Time Monitoring of Yeast Cell Division by Dielectric Spectroscopy", Biophysical Journal, 76, pp. 3345–3348 (1999).

E.K. Balcer–Kubiczek et al., "Expression Analysis of Human HL60 Cells Exposed to 60 Hz Square–or Sine–Wave Magnetic Fields", Radiation Research, 153, pp. 670–678 (2000).

C.A.L. Basset et al., "Beneficial Effects of Electromagnetic Fields", Journal of Cellular Biochemistry, 51, pp. 387–393 (1993).

P. Conti et al., "Effects of Electromagnetic Fields on Several CD Markers and Transcription and Expression of CD4", Immunobiology, 201, pp. 36–48 (1999).

A.M. Gonzalez et al., "Effects of an Electric Field of Sinusoidal Waves on the Amino Acid Biosynthesis by Azotobacter", Z. Naturforsch, 35, pp. 258–261 (1980).

E.M. Goodman et al., "Effects of Electromagnetic Fields on Molecules and Cells", International Review of Cytology, 158, pp. 279–339 (1995).

T. Grospietsch et al., "Stimulating Effects of Modulated 150 MHz Electromagnetic Fields on the Growth of Escherichia coli in a Cavity Resonator", Bioelectrochemistry and Bioenergetics, 37, pp. 17–23 (1995).

W. Grundler et al., "Nonthermal Effects of Millimeter Microwaves on Yeast Growth", Z. Naturforsch, 33, pp. 15–22 (1978).

W. Grundler et al., "Mechanisms of Electromagnetic Interaction with Cellular Systems", Naturwissenschaften, 79, pp. 551–559 (1992).

(List continued on next page.)

Primary Examiner—Christopher R. Tate
Assistant Examiner—Randall Winston
(74) Attorney, Agent, or Firm—Fish & Neave; James F. Haley, Jr.; Z. Ting Li

(57) ABSTRACT

Compositions comprising a plurality of yeast cells, wherein said plurality of yeast cells are characterized by their ability to treat hyperlipemia (e.g., regulate triglyceride and/or beta-lipoprotein levels) in a subject as a result of having been cultured in the presence of an alternating electric field having a specific frequency and a specific field strength. Also included are methods of making such compositions.

9 Claims, 2 Drawing Sheets

OTHER PUBLICATIONS

O.I. Ivaschuk et al., "Exposure of Nerve Growth Factor–Treated PC12 Rat Pheochromocytoma Cells to a Modulated Radiofrequency Field at 836.55 MHz: Effects on c–jun and c–fos Expression", *Bioelectromagnetics*, 18, pp. 223–229 (1997).

F. Jelinek et al., "Microelectronic Sensors for Measurements of Electromagnetic Fields of Living Cells and Experimental Results", *Bioelectrochemistry and Bioenergetics*, 48, pp. 261–266 (1999).

A. Lacy–Hulbert et al., "Biological Response to Electromagnetic Fields", *FASEB Journal*, 12, pp. 395–420 (1998).

C.R. Libertin et al., "Effects of Gamma Rays, Ultraviolet Radiation, Sunlight, Microwaves and Electromagnetic Fields on Gene Expression Mediated by Human Immunodeficiency Virus Promoter", *Radiation Research*, 140, pp. 91–96 (1994).

H. Lin et al., "Specific Region of the c–myc Promoter Is Responsive to Electric and Magnetic Fields", *Journal of Cellular Biochemistry*, 54, pp. 281–288 (1994).

H. Lin et al., "Magnetic Field Activation of Protein–DNA Binding", *Journal of Cellular Biochemistry*, 70, pp. 297–303 (1998).

L.I. Loberg et al., "Expression of Cancer–Related Genes in Human Cells Exposed to 60 Hz Magnetic Fields", *Radiation Research*, 153, pp. 679–684 (2000).

R.L. Moore, "Biological Effects of Magnetic Fields: Studies with Microorganisms", *Canadian Journal of Microbiology*, 25, pp. 1145–1151 (1979).

C.A. Morehouse et al., "Exposure of Daudi Cells to Low–Frequency Magnetic Fields Does Not Elevate MYC Steady–State mRNA Levels", *Radiation Research*, 153, pp. 663–669 (2000).

V. Norris et al., "Do Bacteria Sing? Sonic Intercellular Communication Between Bacteria May Reflect Electromagnetic Intracellular Communication Involving Coherent Collective Vibrational Modes that Could Integrate Enzyme Activities and Gene Expression", *Molecular Microbiology*, 24, pp. 879–880 (1997).

G. Novelli et al., "Study of the Effects of DNA of Electromagnetic Fields Using Clamped Homogeneous Electric Field Gel Electrophoresis", *Biomedicine & Pharmacotherapy*, 45, pp. 451–454 (1991).

J.L. Phillips, "Effects of Electromagnetic Field Exposure on Gene Transcription", *Journal of Cellular Biochemistry*, 51, pp. 381–386 (1993).

V. Romano–Spica et al., "Ets1 Oncogene Induction by ELF–Modulated 50 MHz Radiofrequency Electromagnetic Field", *Bioelectromagnetics*, 21, pp. 8–18 (2000).

J.E. Trosko, "Human Health Consequences of Environmentally–Modulated Gene Expression: Potential Roles of ELF–EMF Induced Epigenetic Versus Mutagenic Mechanisms of Disease", *Bioelectromagnetics*, 21, pp. 402–406 (2000).

C. Ventura et al., "Elf–pulsed Magnetic Fields Modulate Opioid Peptide Gene Expression in Myocardial Cells", *Cardiovascular Research*, 45, pp. 1054–1064 (2000).

A.M. Woodward et al., "Genetic Programming as an Analytical Tool for Non–linear Dielectric Spectroscopy", *Bioelectrochemistry and Bioenergetics*, 48, pp. 389–396 (1999).

T. Yonetani et al., "Electromagnetic Properties of Hemoproteins", *The Journal of Biological Chemistry*, 247, pp. 2447–2455 (1972).

L. Zhang et al., "Electrostimulation of the Dehydrogenase System of Yeast by Alternating Currents", *Bioelectrochemistry and Bioenergetics*, 28, pp. 341–353 (1992).

DIETARY SUPPLEMENTS FOR TREATING HYPERLIPEMIA

FIELD OF THE INVENTION

The invention relates to compositions that can ameliorate or prevent hyperlipemia and are useful as dietary supplements (e.g., health drinks). These compositions contain yeast cells obtainable by growth in electromagnetic fields with specific frequencies and field strengths.

BACKGROUND OF THE INVENTION

Hyperlipemia is a state of higher than normal blood concentration of lipid components, such as cholesterols, neutral fats, phospholipids or free fatty acids that are in the form of water-soluble lipoproteins. Hyperlipemia is caused by abnormal lipoprotein metabolism. A prolonged hyperlipemic status has been linked to diseases of the circulatory system such as arteriosclerosis, myocardial infarction, angina pectoris, cerebral infarction, apoplexy, coronary diseases, cerebrovascular disorders, high blood pressure, and obesity.

Conventional therapeutic agents for the treatment of hyperlipemia include clofibrate, clinofibrate, phenofibrate, bezafibrate and the like, probucol and nicotinic acid. However, the clofibrate-type drugs are accompanied by adverse side effects such as formation of gallstone, muscular disorders, hepatic dysfunctions and gastrointestinal disorders. Moreover, these drugs must be administered in a large quantity to obtain a certain clinical effect. As a result, severe side effects are frequently observed.

SUMMARY OF THE INVENTION

This invention is based on the discovery that certain yeast cells can be activated by electromagnetic fields having specific frequencies and field strengths to produce substances useful in treating hyperlipidemia (for example, regulating triglyceride and/or beta-lipoprotein levels). Compositions comprising these activated yeast cells can therefore be used as dietary supplements, in the form of health drinks or dietary pills (tablets or powder). For instance, these compositions can be used to alleviate (e.g., lower) high blood lipid concentration in a hyperlipemic human, or to prevent or postpone the onset of hyperlipemia in a high risk individual (e.g., someone predisposed to hyperlipemia because of his genetic background or life style).

This invention embraces a composition comprising a plurality of yeast cells that have been cultured in an alternating electric field having a frequency in the range of about 13900 to 14700 MHz (e.g., 14000–14500 MHz) and a field strength in the range of about 160 to 500 mV/cm (e.g., 210–250, 280–320, 320–350, 350–380, 380–420 or 420–450 mV/cm). The yeast cells are cultured for a period of time sufficient to activate said plurality of yeast cells to treat hyperlipemia in a subject. In one embodiment, the frequency and/or the field strength of the alternating electric field can be altered within the aforementioned ranges during said period of time. In other words, the yeast cells are exposed to a series of electromagnetic fields. An exemplary period of time is about 100–200 hours (e.g., 118–149 hours).

Also included in this invention is a composition comprising a plurality of yeast cells that have been cultured under acidic conditions in an alternating electric field having a frequency in the range of about 13900 to 14700 MHz (e.g., 14000–14500 MHz) and a field strength in the range of about 160 to 500 mV/cm (e.g., 380–420 or 410–430 mV/cm). In one embodiment, the yeast cells are exposed to a series of electromagnetic fields. An exemplary period of time is about 30–100 hours (e.g., 61–77 hours).

Yeast cells that can be included in this composition are available from the China General Microbiological Culture Collection Center ("CGMCC"), a depository recognized under the Budapest Treaty (China Committee for Culture Collection of Microorganisms, Institute of Microbiology, Chinese Academy of Sciences, Haidian, P.O. Box 2714, Beijing, 100080, China). Useful yeast species include, but are not limited to, those commonly used in food and pharmaceutical industries, such as *Saccharomyces cerevisiae, Saccharomyces carlsbergensis, Saccharomyces rouxii, Saccharomyces sake, Saccharomyces uvarum*, Saccharomyces sp., *Schizosaccharomyces pombe*, and *Rhodotorula aurantiaca*. For instance, the yeast cells can be of the strain *Saccharomyces carlsbergensis* Hansen AS2.420, AS2.440, AS2.444; *Saccharomyces cerevisiae* Hansen AS2.375, AS2.501, AS2.502, AS2.503, AS2.504, AS2.535, AS2.558, AS2.560, AS2.561, AS2.562, or IFFI1040. Other useful yeast strains are illustrated in Table 1.

This invention further embraces a composition comprising a plurality of yeast cells, wherein said plurality of yeast cells have been activated to treat hypertension in a subject. Included in this invention are also methods of making these compositions.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention. All publications and other references mentioned herein are incorporated by reference in their entirety. In case of conflict, the present specification, including definitions, will control. The materials, methods, and examples are illustrative only and not intended to be limiting. Throughout this specification and claims, the word "comprise," or variations such as "comprises" or "comprising" will be understood to imply the inclusion of a stated integer or group of integers but not the exclusion of any other integer or group of integers. A subject includes a human and veterinary subject.

Other features and advantages of the invention will be apparent from the following detailed description, and from the claims.

DETAILED DESCRIPTION OF THE INVENTION

Figure 1:
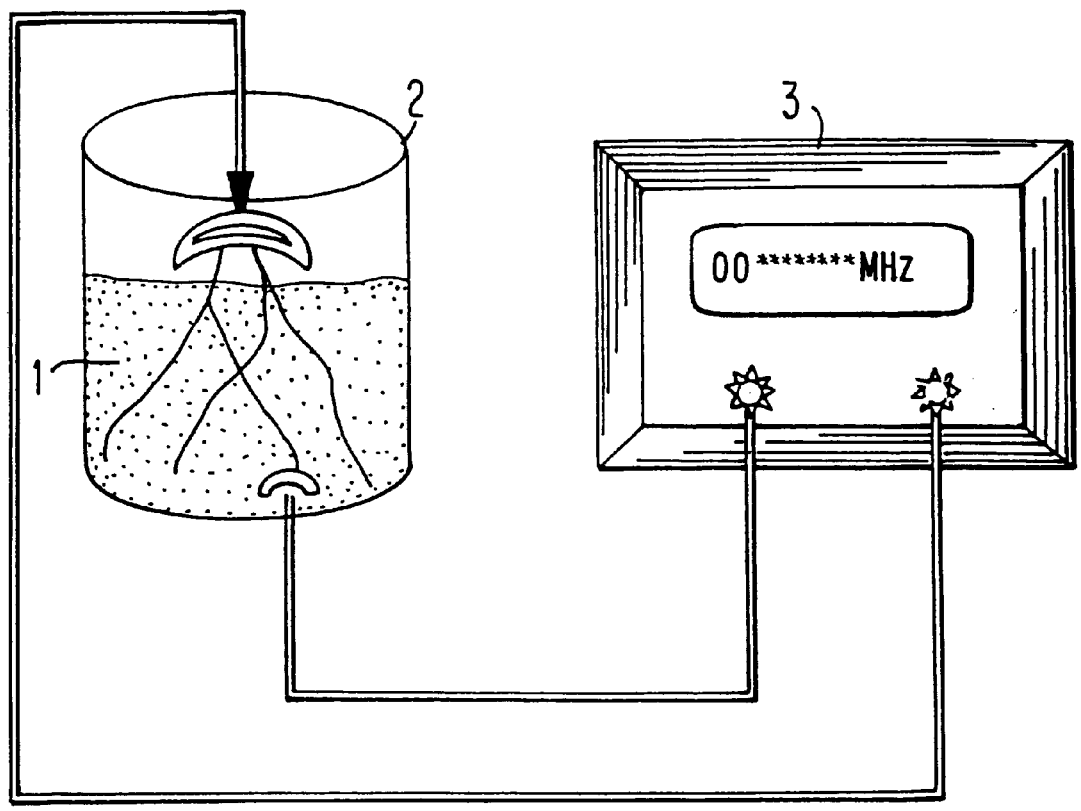
FIG. 1 is a schematic diagram showing an exemplary apparatus for activating yeast cells using electromagnetic fields. 1: yeast culture; 2: container; 3: power supply.

This invention is based on the discovery that certain yeast strains can be activated by electromagnetic fields ("EMF") having specific frequencies and field strengths to become highly efficient in producing substances that lower triglyceride and beta-lipoprotein levels in a subject. Compositions containing these activated yeast cells are useful in the treatment of hyperlipemia. Yeast compositions containing activated yeast cells can be used as dietary supplements, in the form of health drinks or dietary pills (tablets or powder).

Since the activated yeast cells contained in the yeast compositions have been cultured to endure acidic conditions (pH 2.5–4.2), these cells can survive the gastric environment and pass on to the intestines. Once in the intestines, the yeast cells are ruptured by various digestive enzymes, and the anti-hyperlipemic substances are released and readily absorbed.

Without being bound by any theory or mechanism, the inventor believes that EMFs activate or enhance the expression of a gene or a set of genes in yeast cells such that the yeast cells become active or more efficient in performing certain metabolic activities which lead to the desired anti-hyperlipemic effect.

I. Yeast Strains Useful in the Invention

The types of yeasts useful in this invention include, but are not limited to, yeasts of the genera Saccharomyces, *Schizosaccharoinyces pombe* and Rhodotorula.

Exemplary species within the above-listed genera include, but are not limited to, those illustrated in Table 1. Yeast strains useful for this invention can be obtained from laboratory cultures, or from publically accessible culture depositories, such as CGMCC and the American Type Culture Collection, 10801 University Boulevard, Manassas, Va. 20110–2209. Non-limiting examples of useful strains (with accession numbers of CGMCC) are *Saccharomyces carlsbergensis* Hansen AS2.420, AS2.440, AS2.444; *Saccharomyces cerevisiae Hansen* AS2.375, AS2.501, AS2.502, AS2.503, AS2.504, AS2.535, AS2.558, AS2.560, AS2.561, AS2.562, and IFF11048. Other useful yeast strains are illustrated in Table 1.

Although it is preferred, the preparation of the yeast compositions of this invention is not limited to starting with a pure strain of yeast. A yeast composition of the invention may be produced by culturing a mixture of yeast cells of different species or strains. The ability of any activated species or strain of yeasts to treat hyperlipemia can be readily tested by methods known in the art. See, for instance, Examples 1 and 2.

TABLE 1

Exemplary Yeast Strains

*Saccharomyces cerevisiae* Hansen

| ACCC2034 | ACCC2035 | ACCC2036 | ACCC2037 | ACCC2038 |
|---|---|---|---|---|
| ACCC2039 | ACCC2040 | ACCC2041 | ACCC2042 | AS2.1 |
| AS2.4 | AS2.11 | AS2.14 | AS2.16 | AS2.56 |
| AS2.69 | AS2.70 | AS2.93 | AS2.98 | AS2.101 |
| AS2.109 | AS2.110 | AS2.112 | AS2.139 | AS2.173 |
| AS2.174 | AS2.182 | AS2.196 | AS2.242 | AS2.336 |
| AS2.346 | AS2.369 | AS2.374 | AS2.375 | AS2.379 |
| AS2.380 | AS2.382 | AS2.390 | AS2.393 | AS2.395 |
| AS2.396 | AS2.397 | AS2.398 | AS2.399 | AS2.400 |
| AS2.406 | AS2.408 | AS2.409 | AS2.413 | AS2.414 |
| AS2.415 | AS2.416 | AS2.422 | AS2.423 | AS2.430 |
| AS2.431 | AS2.432 | AS2.451 | AS2.452 | AS2.453 |
| AS2.458 | AS2.460 | AS2.463 | AS2.467 | AS2.486 |
| AS2.501 | AS2.502 | AS2.503 | AS2.504 | AS2.516 |
| AS2.535 | AS2.536 | AS2.558 | AS2.560 | AS2.561 |
| AS2.562 | AS2.576 | AS2.593 | AS2.594 | AS2.614 |
| AS2.620 | AS2.628 | AS2.631 | AS2.666 | AS2.982 |
| AS2.1190 | AS2.1364 | AS2.1396 | IFFI1001 | IFFI1002 |
| IFFI1005 | IFFI1006 | IFFI1008 | IFFI1009 | IFFI1010 |
| IFFI1012 | IFFI1021 | IFFI1027 | IFFI1037 | IFFI1042 |

TABLE 1-continued

Exemplary Yeast Strains

| IFFI1043 | IFFI1045 | IFFI1048 | IFFI1049 | IFFI1050 |
|---|---|---|---|---|
| IFFI1052 | IFFI1059 | IFFI1060 | IFFI1062 | IFFI1063 |
| IFFI1202 | IFFI1203 | IFFI1206 | IFFI1209 | IFFI1210 |
| IFFI1211 | IFFI1212 | IFFI1213 | IFFI1214 | IFFI1215 |
| IFFI1220 | IFFI1221 | IFFI1224 | IFFI1247 | IFFI1248 |
| IFFI1251 | IFFI1270 | IFFI1277 | IFFI1287 | IFFI1289 |
| IFFI1290 | IFFI1291 | IFFI1292 | IFFI1293 | IFFI1297 |
| IFFI1300 | IFFI1301 | IFFI1302 | IFFI1307 | IFFI1308 |
| IFFI1309 | IFFI1310 | IFFI1311 | IFFI1331 | IFFI1335 |
| IFFI1336 | IFFI1337 | IFFI1338 | IFFI1339 | IFFI1340 |
| IFFI1345 | IFFI1348 | IFFI1396 | IFFI1397 | IFFI1399 |
| IFFI1411 | IFFI1413 | IFFI1441 | IFFI1443 | |

*Saccharomyces cerevisiae* Hansen Var. ellipsoideus (Hansen) Dekker

| ACCC2043 | AS2.2 | AS2.3 | AS2.8 | AS2.53 |
|---|---|---|---|---|
| AS2.163 | AS2.168 | AS2.483 | AS2.541 | AS2.559 |
| AS2.606 | AS2.607 | AS2.611 | AS2.612 | |

*Saccharomyces chevalieri* Guilliermond

| AS2.131 | AS2.213 |
|---|---|

*Saccharomyces delbrueckii*

AS2.285

*Saccharomyces delbrueckii* Lindner ver. mongolicus (Saito) Lodder et van Rij

| AS2.209 | AS2.1157 |
|---|---|

*Saccharomyces exiguous* Hansen

| AS2.349 | AS2.1158 |
|---|---|

*Saccharomyces fermentati* (Saito) Lodder et van Rij

| AS2.286 | AS2.343 |
|---|---|

*Saccharomyces logos* van laer et Denamur ex Jorgensen

| AS2.156 | AS2.327 | AS2.335 |
|---|---|---|

*Saccharomyces mellis* (Fabian et Quinet) Lodder et kreger van Rij

AS2.195

*Saccharomyces mellis* Microellipsoides Osterwalder

AS2.699

*Saccharomyces oviformis* Osteralder

AS2.100

*Saccharomyces rosei* (Guilliermond) Lodder et Kreger van Rij

AS2.287

*Saccharomyces rouxii* Boutroux

| AS2.178 | AS2.180 | AS2.370 | AS2.371 |
|---|---|---|---|

*Saccharomyces sake* Yabe

ACCC2045

*Candida arborea*

AS2.566

*Candida lambica* (Lindner et Genoud) van. Uden et Buckley

AS2.1182

*Candida krusei* (Castellani) Berkhout

AS2.1045

*Candida lipolytica* (Harrison) Diddens et Lodder

| AS2.1207 | AS2.1216 | AS2.1220 | AS2.1379 | AS2.1398 |
|---|---|---|---|---|
| AS2.1399 | AS2.1400 | | | |

*Candida parapsilosis* (Ashford) Langeron et Talice Var. intermedia Van Rij et Verona

AS2.491

*Candida parapsilosis* (Ashford) Langeron et Talice

AS2.590

TABLE 1-continued

Exemplary Yeast Strains

*Candida pulcherrima* (Lindner) Windisch

AS2.492

*Candida rugousa* (Anderson) Diddens et Lodder

| | | | | |
|---|---|---|---|---|
| AS2.511 | AS2.1367 | AS2.1369 | AS2.1372 | AS2.1373 |
| AS2.1377 | AS2.1378 | AS2.1384 | | |

*Candida tropicalis* (Castellani) Berkhout

| | | | | |
|---|---|---|---|---|
| ACCC2004 | ACCC2005 | ACCC2006 | AS2.164 | AS2.402 |
| AS2.564 | AS2.565 | AS2.567 | AS2.568 | AS2.617 |
| AS2.637 | AS2.1387 | AS2.1397 | | |

*Candida utilis* Henneberg Lodder et Kreger Van Rij

| | | |
|---|---|---|
| AS2.120 | AS2.281 | AS2.1180 |

*Crebrothecium ashbyii* (Guillermond)
Routein (*Eremothecium ashbyii* Guilliemiond)

| | | |
|---|---|---|
| AS2.481 | AS2.482 | AS2.1197 |

*Geotrichum candidum* Link

| | | | | |
|---|---|---|---|---|
| ACCC2016 | AS2.361 | AS2.498 | AS2.616 | AS2.1035 |
| AS2.1062 | AS2.1080 | AS2.1132 | AS2.1175 | AS2.1183 |

*Hansenula anomala* (Hansen)H et P sydow

| | | | | |
|---|---|---|---|---|
| ACCC2018 | AS2.294 | AS2.295 | AS2.296 | AS2.297 |
| AS2.298 | AS2.299 | AS2.300 | AS2.302 | AS2.338 |
| AS2.339 | AS2.340 | AS2.341 | AS2.470 | AS2.592 |
| AS2.641 | AS2.642 | AS2.782 | AS2.635 | AS2.794 |

*Hansenula arabitolgens* Fang

AS2.887

*Hansenula jadinii* (A. et R Sartory Weill et Meyer) Wickerham

ACCC2019

*Hansenula saturnus* (Klocker) H et P sydow

ACCC2020

*Hansenula schneggii* (Weber) Dekker

AS2.304

*Hansenula subpelliculosa* Bedford

| | | | | |
|---|---|---|---|---|
| AS2.740 | AS2.760 | AS2.761 | AS2.770 | AS2.783 |
| AS2.790 | AS2.798 | AS2.866 | | |

*Kloeckera apiculata* (Reess emend. Klocker) Janke

| | | | | |
|---|---|---|---|---|
| ACCC2022 | ACCC2023 | AS2.197 | AS2.496 | AS2.714 |
| ACCC2021 | AS2.711 | | | |

*Lipomycess starkeyi* Lodder et van Rij

| | |
|---|---|
| AS2.1390 | ACCC2024 |

*Pichia farinosa* (Lindner) Hansen

| | | | | |
|---|---|---|---|---|
| ACCC2025 | ACCC2026 | AS2.86 | AS2.87 | AS2.705 |
| AS2.803 | | | | |

*Pichia membranaefaciens* Hansen

| | | | |
|---|---|---|---|
| ACCC2027 | AS2.89 | AS2.661 | AS2.1039 |

*Rhodosporidium toruloides* Banno

ACCC2028

*Rhodotorula glutinis* (Fresenius) Harrison

| | | | | |
|---|---|---|---|---|
| AS2.2029 | AS2.280 | ACCC2030 | AS2.102 | AS2.107 |
| AS2.278 | AS2.499 | AS2.694 | AS2.703 | AS2.704 |
| AS2.1146 | | | | |

*Rhodotorula minuta* (Saito) Harrison

AS2.277

*Rhodotorula rubar* (Demme) Lodder

| | | | | |
|---|---|---|---|---|
| AS2.21 | AS2.22 | AS2.103 | AS2.105 | AS2.108 |
| AS2.140 | AS2.166 | AS2.167 | AS2.272 | AS2.279 |
| AS2.282 | ACCC2031 | | | |

*Rhodotorula aurantiaca* (Saito) Lodder

| | | | | |
|---|---|---|---|---|
| AS2.102 | AS2.107 | AS2.278 | AS2.499 | AS2.694 |
| AS2.703 | AS2.704 | AS2.1146 | | |

*Saccharomyces carlsbergensis* Hansen

| | | | | |
|---|---|---|---|---|
| AS2.113 | ACCC2032 | ACCC2033 | AS2.312 | AS2.116 |
| AS2.118 | AS2.121 | AS2.132 | AS2.162 | AS2.189 |
| AS2.200 | AS2.216 | AS2.265 | AS2.377 | AS2.417 |
| AS2.420 | AS2.440 | AS2.441 | AS2.443 | AS2.444 |
| AS2.459 | AS2.595 | AS2.605 | AS2.638 | AS2.742 |
| AS2.745 | AS2.748 | AS2.1042 | | |

*Saccharomyces uvarum* Beijer

| | | | | |
|---|---|---|---|---|
| IFFI1023 | IFFI1032 | IFFI1036 | IFFI1044 | IFFI1072 |
| IFFI1205 | IFFI1207 | | | |

*Saccharomyces willianus* Saccardo

| | | | | |
|---|---|---|---|---|
| AS2.5 | AS2.7 | AS2.119 | AS2.152 | AS2.293 |
| AS2.381 | AS2.392 | AS2.434 | AS2.614 | AS2.1189 |

*Saccharomyces sp.*

AS2.311

*Saccharomycodes ludwigii* Hansen

| | | |
|---|---|---|
| ACCC2044 | AS2.243 | AS2.508 |

*Saccharomycodes sinenses* Yue

AS2.1395

*Schizosaccharomyces octosporus* Beijerinck

| | |
|---|---|
| ACCC2046 | AS2.1148 |

*Schizosaccharomyces pombe* Lindner

| | | | | |
|---|---|---|---|---|
| ACCC2047 | ACCC2048 | AS2.214 | AS2.248 | AS2.249 |
| AS2.255 | AS2.257 | AS2.259 | AS2.260 | AS2.274 |
| AS2.994 | AS2.1043 | AS2.1149 | AS2.1178 | IFFI1056 |

*Sporobolomyces roseus* Kluyver et van Niel

| | | | | |
|---|---|---|---|---|
| ACCC2049 | ACCC2050 | AS2.19 | AS2.962 | AS2.1036 |
| ACCC2051 | AS2.261 | AS2.262 | | |

*Torulopsis candida* (Saito) Lodder

| | |
|---|---|
| AS2.270 | ACCC2052 |

*Torulopsis famta* (Harrison) Lodder et van Rij

| | |
|---|---|
| ACCC2053 | AS2.685 |

*Torulopsis globosa* (Olson et Hammer) Lodder et van Rij

| | |
|---|---|
| ACCC2054 | AS2.202 |

*Torulopsis inconspicua* Lodder et Kreger van Rij

AS2.75

*Trichosporon behrendii* Lodder et Kreger van Rij

| | |
|---|---|
| ACCC2056 | AS2.1193 |

*Trichosporon capitatum* Diddens et Lodder

| | |
|---|---|
| ACCC2056 | AS2.1385 |

*Trichosporon cutaneum* (de Beurm et al.) Ota

| | | | |
|---|---|---|---|
| ACCC2057 | AS2.25 | AS2.570 | AS2.571 | AS2.1374 |

*Wickerhamia fluorescens* (Soneda) Soneda

| | |
|---|---|
| ACCC2058 | AS2.1388 |

II. Application of Electromagnetic Fields

An electromagnetic field useful in this invention can be generated and applied by various means well known in the art. For instance, the EMF can be generated by applying an alternating electric field or an oscillating magnetic field.

Alternating electric fields can be applied to cell cultures through electrodes in direct contact with the culture medium, or through electromagnetic induction. See, e.g., FIG. 1. Relatively high electric fields in the medium can be generated using a method in which the electrodes are in contact with the medium. Care must be taken to prevent electrolysis at the electrodes from introducing undesired ions into the culture and to prevent contact resistance, bubbles, or other features of electrolysis from dropping the field level below that intended. Electrodes should be matched to their environment, for example, using Ag-AgCl electrodes in solutions rich in chloride ions, and run at as low a voltage as possible. For general review, see Goodman et al., *Effects of EMF on Molecules and Cells*, International Review of Cytology, A Survey of Cell Biology, Vol. 158, Academic Press, 1995.

The EMFs useful in this invention can also be generated by applying an oscillating magnetic field. An oscillating magnetic field can be generated by oscillating electric currents going through Helmholtz coils. Such a magnetic field in turn induces an electric field.

The frequencies of EMFs useful in this invention range from about 13900 to 14700 MHz (e.g., 14000–14050 MHz). Exemplary frequencies are 14023, 14029, 14031, 14037, and 14043 MHz. The field strength of the electric field useful in this invention ranges from about 160 to 500 mV/cm (e.g., 210–250, 280–320, 320–350, 350–380, 380–420 or 420–450 mV/cm). Exemplary field strengths are 220, 223, 308, 316, 322, 330, 332, 364, 406, 420, 422, 428, and 435 mV/cm.

When a series of EMFs are applied to a yeast culture, the yeast culture can remain in the same container while the same set of EMF generator and emitters is used to change the frequency and/or field strength. The EMFs in the series can each have a different frequency or a different field strength; or a different frequency and a different field strength. Such frequencies and field strengths are preferably within the above-described ranges. Although any practical number of EMFs can be used in a series, it may be preferred that the yeast culture be exposed to a total of 2, 3, 4, 5, 6, 7, 8, 9 or 10 EMFs in a series.

Although the yeast cells can be activated after even a few hours of culturing in the presence of an EMF, it may be preferred that the activated yeast cells be allowed to multiply and grow in the presence of the EMF(s) for a total of 40–200 hours (e.g., 60–149 hours).

FIG. 1 illustrates an exemplary apparatus for generating alternating electric fields. An electric field of a desired frequency and intensity is generated by an AC source (3) capable of generating an alternating electric field, preferably in a sinusoidal wave form, in the frequency range of 10 to 20,000 MHz. Signal generators capable of generating signals with a narrower frequency range can also be used. If desirable, a signal amplifier can also be used to increase the output. The activation container (2) can be made from non-conductive metal material, for example, plastics, glass steel, ceramic, and combinations thereof. The wire connecting the activation container (2) and the signal generator (3) is preferably a high frequency coaxial cable with a transmission frequency of at least 30 GHz.

The alternating electric field can be applied to the culture by a variety of means, including placing the yeast culture (1) in close proximity to the signal emitters such as a metal wire or tube capable of transmitting EMFs. The metal wire or tube can be made of red copper, and be placed inside the container (2), reaching as deep as 3–30 cm. For example, if the fluid in the container (2) has a depth of 15–20 cm, 20–30 cm, 30–50 cm, 50–70 cm, 70–100 cm, 100–150 cm or 150–200 cm, the metal wire can be 3–5 cm, 5–7 cm, 7–10 cm, 10–15 cm, 15–20 cm, 20–30 cm and 25–30 cm from the bottom of the container (2), respectively. The number of electrode wires used depends on the volume of the culture as well as the diameter of the wires. The number of metal wires/tubes used can be from 1 to 10 (e.g., 2 to 3). It is recommended, though not mandated, that for a culture having a volume up to 10 L, metal wires/tubes having a diameter of 0.5 to 2.0 mm be used. For a culture having a volume between 10 L and 100 L, metal wires/tubes having a diameter of 3.0 to 5.0 mm can be used. For a culture having a volume in the range of 100–1000 L, metal wires/tubes having a diameter of 6.0 to 15.0 mm can be used. For a culture having a volume greater than 1000 L, metal wires/tubes having a diameter of 20.0 to 25.0 mm can be used.

In one embodiment, the electric field is applied by electrodes submerged in the culture (1). In this embodiment, one of the electrodes can be a metal plate placed on the bottom of the container (2), and the other electrode can comprise a plurality of electrode wires evenly distributed in the culture (1) so as to achieve even distribution of the electric field energy. The number of electrode wires used depends on the volume of the culture as well as the diameter of the wires.

III. Culture Media

Culture media useful in this invention contain sources of nutrients assimilable by yeast cells. Complex carbon-containing substances in a suitable form, such as carbohydrates (e.g., sucrose, glucose, fructose, dextrose, maltose, xylose, cellulose, starches, etc.) and coal, can be the carbon sources for yeast cells. The exact quantity of the carbon sources utilized in the medium can be adjusted in accordance with the other ingredients of the medium. In general, the amount of carbohydrates varies between about 0.1% and 10% by weight of the medium and preferably between about 0.1% and 5% (e.g., about 2%). These carbon sources can be used individually or in combination. Amino acid-containing substances in suitable form (e.g., beef extract and peptone) can also be added individually or in combination. In general, the amount of amino acid containing substances varies between about 0. 1% and 0.5% by weight of the medium and preferably between about 0.1% and 0.3% (e.g., about 0.25%). Among the inorganic salts which can be added to the culture medium are the customary salts capable of yielding sodium, potassium, calcium, phosphate, sulfate, carbonate, and like ions. Non-limiting examples of nutrient inorganic salts are $(NH_4)_2HPO_4$, $KH_2PO_4$, $K_2HPO_4$, $CaCO_3$, $MgSO_4$, $NaCl$, and $CaSO_4$.

IV. Electromagnetic Activation of Yeast Cells

To activate or enhance the ability of yeast cells to produce substances beneficial for the treatment of hyperlipemia (e.g., lowering of triglyceride and/or beta-lipoprotein levels), these cells can be activated by being cultured in an appropriate medium under sterile conditions at 20° C.–38° C., preferably at 28–32° C. (e.g., 30° C.) for a sufficient amount of time, e.g., 100–200 hours (e.g., 118–149 hours), in an alternating electric field or a series of alternating electric fields as described above.

An exemplary culture medium is made by mixing 1000 ml of distilled water with 20 g of sucrose, 30 μg of vitamin $B_3$, 60 μg of vitamin H, 30 μg of vitamin $B_{12}$, 0.20 g of $KH_2PO_4$, 0.2 g of $MgSO_4.7H_2O$, 0.25 g of NaCl, 0.1 g $CaSO_4.2H_2O$, 3.0 g of $CaCO_3.5H_2O$, and 2.5 g of peptone.

An exemplary set-up of the culturing process is depicted in FIG. 1. Untreated yeast cells are added to a culture medium at $1\times10^8$ cells per 1000 ml of the culture medium.

The yeast cells may be *Saccharomyces cerevisiae* Hansen AS2.562, or may be selected from any of the strains listed in Table 1. An exemplary activation process of the yeast cells involves the following sequence: the yeast cells are grown in the culture medium for 38–42 hours (e.g., 40 hours) at 28–32° C. and then exposed to (1) an alternating electric field having a frequency of 14023 MHz and a field strength in the range of 280–320 mV/cm (e.g., 308 mV/cm) for 16–22 hours (e.g., 17 hours); (2) then to an alternating electric field having a frequency of 14029 MHz and a field strength in the range of 280–320 mV/cm (e.g., 316 mV/cm) for 16–22 hours (e.g., 20 hours); (3) then to an alternating electric field having a frequency of 14031 MHz and a field strength in the range of 350–380 mV/cm (e.g., 364 mV/cm) for 20–25 hours (e.g., 23 hours); (4) then to an alternating electric field having a frequency of 14037 MHz and a field strength in the range of 420–450 mV/cm (e.g., 435 mV/cm) for 16–22 hours (e.g., 21 hours); and (5) finally to an alternating electric field having a frequency of 14043 MHz and a field strength in the range of 420–450 mV/cm (e.g., 422 mV/cm) for 12–16 hours (e.g., 14 hours). The activated yeast cells are then recovered from the culture medium by various methods known in the art, dried (e.g., by lyophilization) and stored at about 4° C. in powder form. The resultant yeast powder preferably contains more than $10^{10}$ cells/g.

Subsequently, the activated yeast cells can be measured for their ability to treat hyperlipemia using standard methods known in the art, such as those described in Section VII.

V. Acclimatization of Yeast Cells to the Gastric Environment

Because the activated yeast cells of this invention must pass through the stomach before reaching the small intestine, where the effective components are released from these yeast cells, it is preferred that these yeasts be cultured under acidic conditions so as to acclimatize the cells to the gastric juice. This acclimatization process results in better viability of the yeast cells in the acidic gastric environment.

To achieve this, the yeast powder containing activated yeast cells can be mixed with a highly acidic acclimatizing culture medium at 10 g (containing more than $10^{10}$ activated cells per gram) per 1000 ml. The yeast mixture can then be cultured first in the presence of an alternating electric field having a frequency of 14037 MHz and a field strength in the range of 380–420 mV/cm (e.g., 406 mV/cm) at about 28 to 32° C. for 36–42 hours (e.g., 38 hours). The resultant yeast cells can then be further incubated in the presence of an alternating electric field having a frequency of 14043 MHz and a field strength in the range of 410–430 mV/cm (e.g., 420 mV/cm) at about 28 to 32° C. for 25–35 hours (e.g., 30 hours). The resulting acclimatized yeast cells are then recovered from the culture medium by various methods known in the art and are either dried and stored in powder form ($\geq 10^{10}$ cells/g) at room temperature or stored in vacuum at 0–4° C.

An exemplary acclimatizing culture medium is made by mixing 700 ml fresh pig gastric juice and 300 ml wild Chinese hawthorn extract. The pH of acclimatizing culture medium is adjusted to 2.5 with 0.1 M hydrochloric acid (HCl) and 0.2 M potassium biphthalate ($C_6H_4(COOK)COOH$). The fresh pig gastric juice is prepared as follows. At about 4 months of age, newborn Holland white pigs are sacrificed, and the entire contents of their stomachs are retrieved and mixed with 2000 ml of water under sterile conditions. The mixture is then allowed to stand for 6 hours at 4° C. under sterile conditions to precipitate food debris. The supernatant is collected for use in the acclimatizing culture medium. To prepare the wild Chinese hawthorn extract, 500 g of fresh wild Chinese hawthorn is dried under sterile conditions to reduce water content ($\leq 8\%$). The dried fruit is then ground ($\geq 20$ mesh) and added to 1500 ml of sterile water. The hawthorn slurry is allowed to stand for 6 hours at 4° C. under sterile conditions. The hawthorn supernatant is collected to be used in the acclimatizing culture medium.

VI. Manufacture of Yeast Compositions

Figure 2:
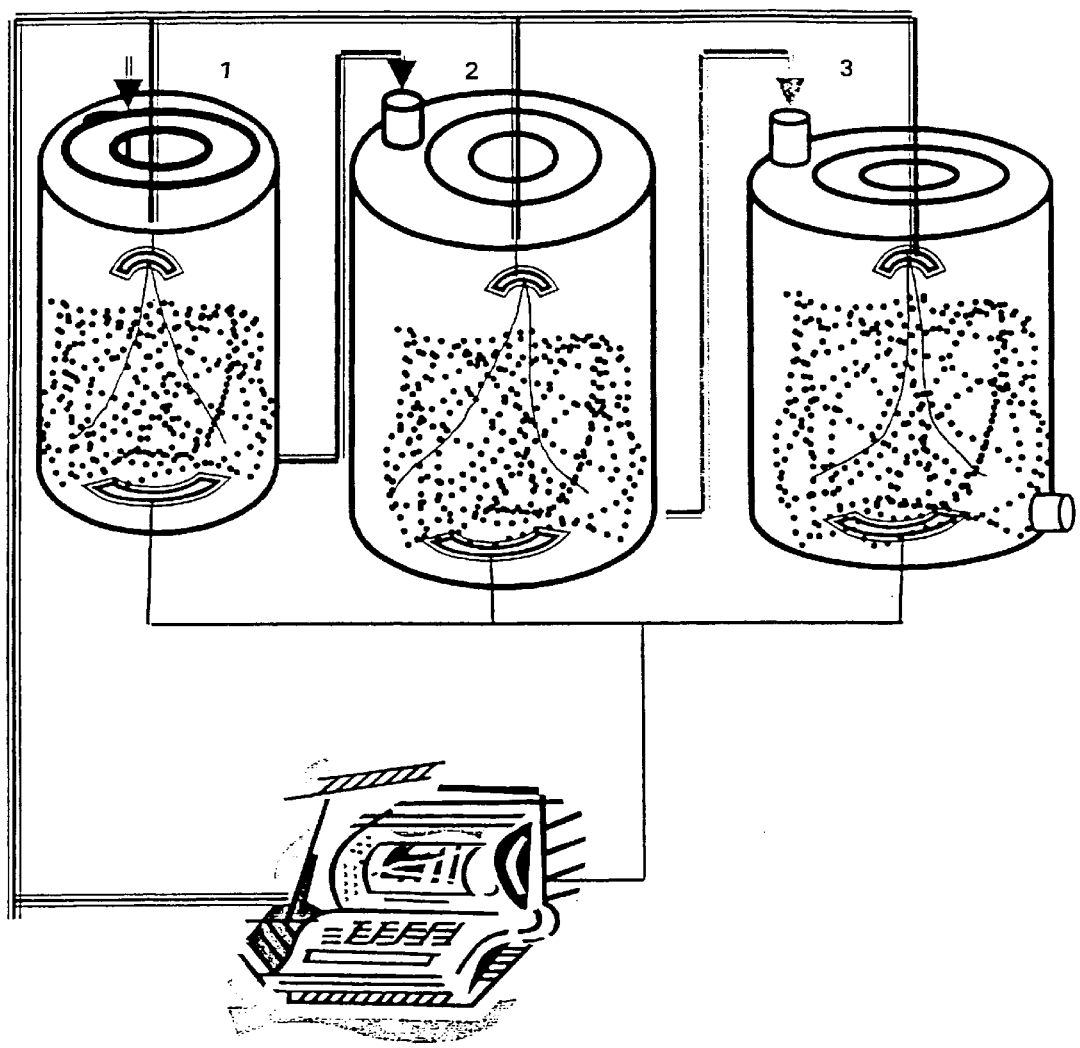
FIG. 2 is a schematic diagram showing an exemplary apparatus for making yeast compositions of the invention. The apparatus comprises a signal generator and interconnected containers 1, 2 and 3.

To prepare the yeast compositions of the invention, an apparatus depicted in FIG. 2 or an equivalent thereof can be used. This apparatus includes three containers, a first container (1), a second container (2), and a third container (3), each equipped with a pair of electrodes (4). One of the electrodes is a metal plate placed on the bottom of the containers, and the other electrode comprises a plurality of electrode wires evenly distributed in the space within the container to achieve even distribution of the electric field energy. All three pairs of electrodes are connected to a common signal generator.

The culture medium used for this purpose is a mixed fruit extract solution containing the following ingredients per 1000 L: 300 L of wild Chinese hawthorn extract, 300 L of jujube extract, 300 L of *Schisandra chinensis* (Turez) Baill seeds extract, and 100 L of soy bean extract. To prepare hawthorn, jujube and *Schisandra chinensis* (Turez) Baill seeds extracts, the fresh fruits are washed and dried under sterile conditions to reduce the water content to no higher than 8%. One hundred kilograms of the dried fruits are then ground ($\geq 20$ mesh) and added to 400 L of sterile water. The mixtures are stirred under sterile conditions at room temperature for twelve hours, and then centrifuged at 1000 rpm to remove insoluble residues. To make the soy bean extract, fresh soy beans are washed and dried under sterile conditions to reduce the water content to no higher than 8%. Thirty kilograms of dried soy beans are then ground into particles of no smaller than 20 mesh, and added to 130 L of sterile water. The mixture is stirred under sterile conditions at room temperature for twelve hours and centrifuged at 1000 rpm to remove insoluble residues. Once the mixed fruit extract solution is prepared, it is autoclaved at 121° C. for 30 minutes and cooled to below 40° C. before use.

One thousand grams of the activated yeast powder prepared as described above (Section V, supra) is added to 1000 L of the mixed fruit extract solution, and the yeast solution is transferred to the first container (1) shown in FIG. 2. The yeast cells are then cultured in the presence of an alternating electric field having a frequency of 14037 MHz and a field strength of about 420–450 mV/cm (e.g., 435 mV/cm) at 28–32° C. under sterile conditions for 12 hours. The yeast cells are further incubated in an alternating electric field having a frequency of 14043 MHz and a field strength of 420–450 mV/cm (e.g., 428 mV/cm). The culturing continues for another 10 hours.

The yeast culture is then transferred from the first container (1) to the second container (2) (if need be, a new batch of yeast culture can be started in the now available the first container (1)), and subjected to an alternating electric field having a frequency of 14037 MHz and a field strength of 320–350 mV/cm (e.g., 332 mV/cm) for 14 hours. Subsequently the frequency and field strength of the electric field are changed to 14043 MHz and 320–340 mV/cm (e.g., 330 mV/cm), respectively. The culturing process continues for another 11 hours.

The yeast culture is then transferred from the second container (2) to the third container (3), and subjected to an alternating electric field having a frequency of 14037 MHz and a field strength of 210–250 mV/cm (e.g., 223 mV/cm)

for 18 hours. Subsequently the frequency and field strength of the electric field are changed to 14043 MHz and 210–230 mV/cm (e.g., 220 mV/cm), respectively. The culturing continues for another 12 hours.

The yeast culture from the third container (3) can then be packaged into vacuum sealed bottles for use as dietary supplement. The compositions may conveniently be formulated as health drinks. If desired, the final yeast culture can also be dried within 24 hours and stored in powder form. The dietary supplement can be taken three to four times daily at 30–60 ml per dose for a three-month period, preferably 10–30 minutes before meals and at bedtime.

In some embodiments, the compositions of the invention can also be administered intravenously or peritoneally in the form of a sterile injectable preparation. Such a sterile preparation can be prepared as follows. A sterilized health drink composition is first treated under ultrasound (1000 Hz) for 10 minutes and then centrifuged at 4355 g for another 10 minutes. The resulting supernatant is adjusted to pH 7.2–7.4 using 1 M NaOH and subsequently filtered through a membrane (0.22 μm for intravenous injection and 0.45 Rm for peritoneal injection) under sterile conditions. The resulting sterile preparation is submerged in a 35–38° C. water bath for 30 minutes before use.

The yeast compositions of the present invention are derived from yeasts used in food and pharmaceutical industries. The yeast compositions are thus devoid of side effects associated with many conventional pharmaceutical compounds.

VII. EXAMPLES

In order that this invention be more fully understood, the following examples are set forth. These examples are for the purpose of illustration only and are not to be construed as limiting the scope of the invention in any way.

The activated yeast compositions used in the following examples were prepared as described above, using Saccharomyces cerevisiae Hansen AS2.562 cells, cultured in the presence of an alternating electric field having the electric field frequency and field strength exemplified in the parentheses following the recommended ranges listed in Section IV, supra. Control (i.e., untreated) yeast compositions were those prepared in the same manner as described in Section VI, supra, except that the yeast cells were cultured in the absence of EMFs. All compositions of interest were administered to the animals by intragastric feeding, unless otherwise specified.

Example 1

Effects of the Treatment on Triglyceride Levels

To test the ability of the activated yeast compositions to control hyperlipemia, thirty healthy hybrid domesticated rabbits (1.8–2.5 kg, half of them male and half of them female, 90–150 days old) were randomly divided into three groups, Group A, B and C. After given regular rabbit feed for three weeks, a mixture of 0.2 mg cholesterol+2 ml lard and a composition of interest at a dosage of 2 ml/kg were administered to each rabbit once daily for eight consecutive weeks. Rabbits in Group A, B and C were given the activated yeast composition, the control yeast composition and saline, respectively, in addition to cholesterol and lard.

On day one of the administration of the mixture, as well as at 2, 4, 6 and 8 weeks after the administration, blood samples were taken from the marginal vein of an ear of the rabbit and centrifuged at 3000 rpm to recover sera. The amounts of serum triglycerides were measured by the method described in Table 2 below.

TABLE 2

A Method for Determining Triglycerides Concentration.

| | Contents in Each Test Tube | | |
|---|---|---|---|
| Steps | Blank Control Tube (ml) | Standard Tube (ml) | Sample Tube (ml) |
| Mix Serum, Triglyceride Standard Solution, (1.0 mg/ml) | — | — | 0.2 |
| | — | 0.2 | — |
| Distilled Water (ml) | 0.2 | 0.2 | — |
| with the Extracting Solvent (1:1 v/v n-heptane/i-PrOH) | 2.2 | 2.0 | 2.0 |
| Shook vigorously so that triglycerides dissolved in the extracting solvent | | | |
| Add $H_2SO_4$ (0.04 M) | 0.5 | 0.5 | 0.5 |
| Shook vigorously for a few seconds and allowed the mixture to separate to two layers | | | |
| Resulting Top Layer | 0.4 | 0.4 | 0.4 |
| Add 5% K0H | 2.0 | 2.0 | 2.0 |
| Stirred in a 65° C. water bath for 5 minutes to allow saponification | | | |
| Add $NaIO_4$ (0.2 M) | 1.0 | 1.0 | 1.0 |
| The mixture was stirred | | | |
| Add Acetylicetone (0.5 M) | 1.0 | 1.0 | 1.0 |
| Stirred in a 65° C. water bath for 10 minutes and cooled to room temperature. Readings of the sample and standard tubes were taken with a spectrophotometer at 420 nm (calibrated with the blank control tube). | | | |

A standard curve of triglyceride was established and the concentration of triglyceride in the samples was determined according to the standard curve. The results were shown in Table 3.

TABLE 3

Effects on Triglyceride Concentration

| | Triglycerides (mg/100 ml) | | | | |
|---|---|---|---|---|---|
| Group | Day 1 | 2 weeks | 4 weeks | 6 weeks | 8 weeks |
| A | 14.02 ± 1.56 | 14.98 ± 1.23 | 15.63 ± 5.23 | 17.12 ± 4.56 | 18.56 ± 4.65 |
| B | 14.85 ± 1.65 | 15.02 ± 1.89 | 25.12 ± 3.21 | 37.85 ± 4.34 | 61.57 ± 5.67 |
| C | 14.21 ± 2.32 | 15.23 ± 1.68 | 25.64 ± 3.45 | 38.24 ± 5.36 | 60.58 ± 8.95 |

The above results show that the activated yeast composition was more effective in lowering the triglyceride levels than the control yeast composition.

Example 2

Effects of the Treatment on β-Lipoprotein Levels

Blood samples were prepared as described in Example 1. The levels of serum beta-lipoprotein were measured by nephelometry as described in Table 4. The beta-lipoprotein concentration was calculated based on a standard curve and the results were tabulated in Table 5.

TABLE 4

Method for Measuring Serum Beta-Lipoprotein Level

| Steps | Contents in Each Tube | |
| --- | --- | --- |
| | Blank Control Tube (ml) | Sample Tube (ml) |
| Mix Serum with | — | 0.3 |
| 0.85% NaCl | 4.8 | 4.5 |
| Heparin Solution* | 1.2 | 1.2 |
| 0.25M MnCl$_2$ | 0.6 | 0.6 |

Mixed well and allowed to stand for 10 minutes. Readings of the sample tube were taken at 560 nm (calibrated with the blank control) with a nephelometer.
*The heparin solution was prepared by mixing 50 mg of heparin and 100 ml of water and stored in refigeration.

TABLE 5

Effects of Treatment on Beta-Lipoprotein Level

| | beta-Lipoprotein (mg/100 ml) | | | | |
| --- | --- | --- | --- | --- | --- |
| Group | Day 1 | 2 weeks | 4 weeks | 6 weeks | 8 weeks |
| A | 214.2± 45.5 | 1002.2± 89.3 | 1013.4± 98.5 | 1008.9± 78.4 | 1004.8± 142.6 |
| B | 240.0± 32.4 | 1239.2± 142.3 | 1522.3± 92.7 | 1728.7± 114.2 | 1922.8± 152.6 |
| C | 232.3± 42.2 | 1245.0± 82.5 | 1452.6± 78.6 | 1632.7± 92.7 | 1895.6± 112.5 |

The above results show that the activated yeast composition was more effective in lowering the beta-lipoprotein levels than the control yeast composition.

While a number of embodiments of this invention have been set forth, it is apparent that the basic constructions may be altered to provide other embodiments which utilize the compositions and methods of this invention.

What is claimed is:

1. A composition comprising a plurality of yeast cells, wherein said plurality of yeast cells are characterized by their ability to treat hyperlipemia in a subject, said ability resulting from their having been cultured in the presence of an alternating electric field having a frequency in the range of 13900 to 14700 MHz and a field strength in the range of 160 to 500 mV/cm, as compared to yeast cells not having been so cultured.

2. The composition of claim 1, wherein said frequency is in the range of 14023 to 14043 MHz.

3. The composition of claim 1, wherein said field strength is in the range of 210–250, 280–320, 320–350, 350–380, 380–420 or 420–450 mV/cm.

4. The composition of claim 1, wherein said yeast cells are cells of the species *Saccharomyces cerevisiae, Saccharomyces carlsbergensis, Saccharomyces rouxii, Saccharomyces sake, Saccharomyces uvarum,* Saccharomyces sp., *Schizosaccharomyces pombe,* or *Rhodotorula aurantiaca.*

5. The composition of claim 1, wherein said yeast cells are cells of the strain deposited at the China General Microbiological Culture Collection Center with an accession number selected from the group consisting of AS2.420, AS2.440, AS2.444, AS2.375, AS2.501, AS2.502, AS2.503, AS2.504, AS2.535, AS2.558, AS2.560, AS2.561, AS2.562, and IFFI1048.

6. The composition of claim 1, wherein said composition is in the form of a tablet, powder, or a health drink.

7. The composition of claim 6, wherein said composition is in the form of a health drink.

8. A method of preparing a yeast composition, comprising culturing a plurality of yeast cells in the presence of an alternating electric field having a frequency in the range of 13900 to 14700 MHz and a field strength in the range of 160 to 500 mV/cm, wherein said composition is capable of treating hyperlipemia in a subject, as compared to yeast cells not having been so cultered.

9. A method for treating hyperlipemia in a subject comprising orally administering to said subject a composition of claim 1.

* * * * *